(12) United States Patent
Uber, III

(10) Patent No.: US 10,369,276 B2
(45) Date of Patent: Aug. 6, 2019

(54) ACCURATELY DELIVERING PARTIAL DOSES OF A DRUG POST DILUTION USING AN INJECTOR

(71) Applicant: BAYER HEALTHCARE LLC, Indianola, PA (US)

(72) Inventor: Arthur E. Uber, III, Pittsburgh, PA (US)

(73) Assignee: Bayer HealthCare LLC, Whippany, NJ (US)

( * ) Notice: Subject to any disclaimer, the term of this patent is extended or adjusted under 35 U.S.C. 154(b) by 419 days.

(21) Appl. No.: 15/037,515

(22) PCT Filed: Nov. 25, 2014

(86) PCT No.: PCT/US2014/067429
§ 371 (c)(1),
(2) Date: May 18, 2016

(87) PCT Pub. No.: WO2015/077777
PCT Pub. Date: May 28, 2015

(65) Prior Publication Data
US 2016/0279324 A1    Sep. 29, 2016

Related U.S. Application Data

(60) Provisional application No. 61/908,321, filed on Nov. 25, 2013.

(51) Int. Cl.
*A61M 5/145* (2006.01)
*A61M 5/168* (2006.01)
(Continued)

(52) U.S. Cl.
CPC .... *A61M 5/14546* (2013.01); *A61M 5/16827* (2013.01); *A61M 5/007* (2013.01);
(Continued)

(58) Field of Classification Search
CPC ........ A61M 2005/14292; A61M 5/007; A61M 5/1411; A61M 5/142; A61M 5/14546; A61M 5/16827; A61M 5/178; A61M 5/20
See application file for complete search history.

(56) References Cited

U.S. PATENT DOCUMENTS 4,348,283 A    9/1982  Ash
5,383,858 A    1/1995  Reilly et al.
(Continued)

FOREIGN PATENT DOCUMENTS

WO    2012155035 A1    11/2012
WO    2014144651 A2    9/2014

OTHER PUBLICATIONS

"Extended European Search Report from EP Application No. EP14864966", dated May 11, 2017.
(Continued)

*Primary Examiner* — Brandy S Lee
(74) *Attorney, Agent, or Firm* — Joseph L. Kent; David Schramm; James R. Stevenson

(57) ABSTRACT

Methods and systems for diluting a dose of a substance to be delivered to a patient and for determining a maximum deliverable dose of the substance and/or a partial fluid volume to be delivered to the patient to provide a desired dose amount are provided. The method includes the step of providing a first substance within a fluid reservoir having an initial unit value. The method also includes diluting the first substance with a second substance to produce the diluted solution. Once the first substance is diluted, a total volume (VTotal) of the diluted solution is measured. A concentration of the diluted solution is then calculated based on the initial unit value and the total volume (VTotal). A fluid delivery system including a fluid reservoir and fluid delivery device, which is configured to perform the method, is also provided.

20 Claims, 9 Drawing Sheets

(51) Int. Cl.
*A61M 5/142* (2006.01)
*A61M 5/00* (2006.01)
*A61M 5/14* (2006.01)
*A61M 5/178* (2006.01)
*A61M 5/20* (2006.01)

(52) U.S. Cl.
CPC ........... *A61M 5/142* (2013.01); *A61M 5/1411* (2013.01); *A61M 5/178* (2013.01); *A61M 5/20* (2013.01); *A61M 2005/14292* (2013.01)

(56) References Cited

U.S. PATENT DOCUMENTS

| | | | |
|---|---|---|---|
| 7,553,294 | B2 | 6/2009 | Lazzaro et al. |
| 7,666,169 | B2 | 2/2010 | Cowan et al. |
| 2008/0045834 | A1* | 2/2008 | Uber .................. A61B 8/06 600/431 |
| 2008/0169045 | A1* | 7/2008 | Tribble .................. B65B 3/003 141/1 |
| 2013/0000250 | A1 | 1/2013 | Tribble et al. |
| 2013/0079581 | A1 | 3/2013 | Agamaite et al. |
| 2013/0079582 | A1* | 3/2013 | Della Rocca .......... A61K 39/39 600/13 |
| 2013/0124103 | A1* | 5/2013 | Mabie .................... G01T 1/167 702/23 |
| 2014/0027009 | A1 | 1/2014 | Riley et al. |

OTHER PUBLICATIONS

"International Preliminary Report on Patentability and Written Opinion from PCT/US2014/067429 dated Jun. 9, 2016", dated Jun. 9, 2016.

"International Search Report from PCT/US2014/067429 dated Feb. 11, 2015", dated Feb. 11, 2015.

* cited by examiner

| | A | B | C | D | E | F | G |
|---|---|---|---|---|---|---|---|
| 1 | | | | | | | |
| 2 | | Dosing with Dilution | | Not accounting for dead volume | | | |
| 3 | | | | | | | |
| 4 | Initial Volume of drug (Vdrug) | 2 ml | | | 2 ml | | |
| 5 | Initial Dose | 9 mg | | | 9 mg | | |
| 6 | Initial Concentration | 4.5 mg/ml | | | 4.5 mg/ml | | |
| 7 | Volume of Diluent (Vdiluent) | 9 ml | | | 9 ml | | |
| 8 | Total Volume (Vtotal) | 11 ml | | | 11 ml | | |
| 9 | | | | | | | |
| 10 | | | | | | | |
| 11 | Volume in syringe after purging (Vdeliverable) | 10 ml | | | 10 ml | | |
| 12 | dead volume in neck & valve | 1 ml | | | 0 ml | | |
| 13 | Total Volume (Vtotal) | 11 | | | 10 | | |
| 14 | Diluted concentration | 0.82 mg/ml | | | 0.90 mg/ml | | |
| 15 | Maximum Deliverable Dose | 8.18 mg | | | 9.00 mg | | |
| 16 | Dose desired | 5 mg | | | 5 mg | | |
| 17 | Volume to be delivered | 6.11 ml | | | 5.56 ml | | |
| 18 | Dose Delivered (check) | 5 mg | | | 4.55 mg | | |
| 19 | | | | | -9% % error | | |
| 20 | | | | | | | |
| 21 | | | | | | | |
| 22 | Half-life | 6:00:21 | time (military format) | | | | |
| 23 | Time when Initial Dose was measured | 10:30:00 | | | | | |
| 24 | Time Change Increment | 1:00:00 | | | | | |
| 25 | Decay in time increment | 0.891 | elapsed time | Volume to inject | | Max Activity Check | |
| 26 | Start time | 11:00:00 | 0:30:00 | 6.47 ml | | 5 | mCi |
| 27 | Times to Change | 12:00:00 | 1:30:00 | 7.27 ml | | 5 | mCi |
| 28 | Times to Change | 13:00:00 | 2:30:00 | 8.16 ml | | 5 | mCi |
| 29 | Times to Change | 14:00:00 | 3:30:00 | 9.15 ml | | 5 | mCi |
| 30 | Times to Change | 15:00:00 | 4:30:00 | 10.00 ml | | 4.87 | mCi |

| | A | B | C |
|---|---|---|---|
| 1 | | | |
| 2 | | | |
| 3 | | Dosing with Dilution | |
| 4 | Initial Volume of drug (Vdrug) | 2 | ml |
| 5 | Initial Dose | 9 | mg |
| 6 | Initial Concentration | =B5/B4 | mg/ml |
| 7 | Volume of Diluent (Vdiluent) | 9 | ml |
| 8 | Total Volume (Vtotal) | =B7+B4 | ml |
| 9 | | | |
| 10 | | | |
| 11 | Volume in syringe after purging (Vdeliverable) | 10 | ml |
| 12 | dead volume in neck & valve | 1 | ml |
| 13 | Total Volume (Vtotal) | =B12+B11 | |
| 14 | Diluted concentration | =B5/B13 | mg/ml |
| 15 | Maximum Deliverable Dose | =B5*B11/B13 | mg |
| 16 | Dose desired | 5 | mg |
| 17 | Volume to be delivered | =B16/B14 | ml |
| 18 | Dose Delivered (check) | =B17*B14 | mg |
| 19 | | | |
| 20 | | | |
| 21 | Half-life | 0.2502430555555 | time |
| 22 | Time when Initial Dose was measured | 0.4375 | |
| 23 | Time Change Increment | 0.04166666666 | |
| 24 | Decay in time increment | =2^(-B24/B22) | |
| 25 | | | |
| 26 | Start time | 0.458333333333 | elapsed time |
| 27 | Times to Change | =B26+B24 | =B26-B$23 |
| 28 | Times to Change | =B27+B$24 | =B27-B$23 |
| 29 | Times to Change | =B28+B$24 | =B28-B$23 |
| 30 | Times to Change | =B29+B$24 | =B29-B$23 |
| | | | =B30-B$23 |

(A)

| | D | E | F | G |
|---|---|---|---|---|
| | Volume to Inject | Not Accounting for Dead Volume | | |
| | | 2 | ml | |
| | | 9 | mg | |
| | | =E5/E4 | mg/ml | |
| | | 9 | ml | |
| | | =E7+E4 | ml | |
| | | | | |
| | | 10 | ml | |
| | | 0 | ml | |
| | | =E12+E11 | ml | |
| | | =E5/E13 | mg/ml | |
| | | =E5*E11/E13 | mg | |
| | | 5 | mg | |
| | | =E16/E14 | ml | |
| | | =E17*E14 | mg | |
| | | =(E18/B18)-1 | % error | |
| | | | | |
| | | | | |
| | | | Max Activity Check | |
| =MIN(B$16/((B$14)^2^(-C26/B$22)), B$11) | ml | =D26*B$14^2^(-C26/B$22) | mCi |
| =MIN(B$16/((B$14)^2^(-C27/B$22)), B$11) | ml | =D27*B$14^2^(-C27/B$22) | mCi |
| =MIN(B$16/((B$14)^2^(-C28/B$22)), B$11) | ml | =D28*B$14^2^(-C28/B$22) | mCi |
| =MIN(B$16/((B$14)^2^(-C29/B$22)), B$11) | ml | =D29*B$14^2^(-C29/B$22) | mCi |
| =MIN(B$16/((B$14)^2^(-C30/B$22)), B$11) | ml | =D30*B$14^2^(-C30/B$22) | mCi |

FIG. 3C

ACCURATELY DELIVERING PARTIAL DOSES OF A DRUG POST DILUTION USING AN INJECTOR

CROSS-REFERENCE TO RELATED APPLICATIONS

This application is a 371 national phase application of PCT International Application No. PCT/US2014/067429, filed Nov. 25, 2014 and designating the United States of America, which claims priority to U.S. Provisional Application No. 61/908,321, filed on Nov. 25, 2013, the disclosures of each of which are incorporated herein by reference in their entirety.

BACKGROUND OF THE DISCLOSURE

Field of the Disclosure

This disclosure relates to methods and systems for diluting a dose of a substance to be delivered to a patient and for determining a maximum deliverable dose of the substance and/or a partial fluid volume to be delivered to the patient to provide a desired dose amount.

Description of Related Art

Many medical procedures require the delivery of a fluid to the patient. Most of the time, the full volume of fluid provided is injected into the patient, with some fluid volume remaining in the fluid reservoir or fluid path. This remaining amount is commonly called the priming volume, dead space volume, retained volume, or non-deliverable volume. This priming volume is often insignificant because it is either small compared to the total volume being delivered or because extra fluid is provided and only the prescribed volume is delivered to the patient. Any extra fluid, including the priming volume, is thrown away after the delivery of the prescribed, desired, or programmed volume is completed. This procedure works well when the fluid is a known, consistent concentration and the prescription is for a volume which is less than the total provided or initial volume.

In some cases, such as nuclear medicine, biologic treatments, or cell therapies, the fluid volumes provided or to be injected are small enough that the dead volume in the fluid path or container may be significant. In nuclear medicine it is common to measure the residual dose in the syringe, needle, and other fluid path elements after the fact, and record that information on the patient's chart along with the initial dose, so that it is possible to compute the delivered dose at a later point in time if it becomes necessary. One approach to improve this situation is to dilute the fluid so that the total volume is increased sufficiently to increase the deliverable amount of the medicine or agent. It then becomes a challenge to know what volume to inject if the whole diluted volume is not to be injected at one time. It also is a challenge to know the total dose that could possibly be injected given the existence of dead space in the fluid path. Specifically, the post dilution concentration of the diluted drug depends upon the initial volume of the drug and the volume of the diluent. An apparatus and system for injecting a small volume of a therapeutic or contrast agent to a patient is discussed in PCT Application No. PCT/US2014/029152 to Uram et al. (published as Publication No. WO 2014/144651), which is assigned to the assignee of the present application, and the disclosure of which is incorporated by reference in its entirety.

SUMMARY OF THE DISCLOSURE

In view of the challenges in preparing and/or injecting a diluted fluid solution from a small amount of a therapeutic agent or drug, it is desirable to provide a system and method to enable a health professional to inject a desired amount of a drug into a patient, preferably while enabling dilution and/or accounting for dead volume in the fluid delivery path.

According to an aspect of the disclosure, a method of determining a concentration of a diluted solution in a fluid reservoir may be provided. The method may include providing a first substance within the reservoir having an initial dose value and an unknown volume. The method may also include diluting the first substance with a second substance to produce the diluted solution. Once the first substance is diluted, a total volume ($V_{Total}$) of the diluted solution may be measured. A concentration of the diluted solution may be then calculated based on the initial unit value and the total volume ($V_{Total}$).

According to another aspect of the disclosure, a method for determining a maximum deliverable dose within a reservoir may be provided. The method may include providing a first substance within the reservoir having an initial dose value and introducing a second substance to the reservoir. Once the substances are mixed together, a total volume ($V_{Total}$) consisting of a volume of the first substance and a volume of the second substance may be determined. A maximum deliverable dose within the reservoir may be then calculated based on a current dose value and a ratio of a deliverable volume ($V_{Deliverable}$) and the total volume ($V_{Total}$).

According to another aspect of the disclosure, a method of calculating a diluted dose volume ($V_{Dose}$) of a diluted substance to be delivered to a patient may be provided. The method may include providing a first substance within a reservoir having an initial dose value and introducing a second substance to the reservoir. Once the substances are introduced to the reservoir, a total volume ($V_{Total}$) consisting of a volume of the first substance and a volume of the second substance may be determined. A dose volume ($V_{Dose}$) based on a desired actual dose value of the first substance, a current dose value, and the total volume ($V_{Total}$) may be then calculated.

According to another aspect of the disclosure, a method of delivering a diluted partial dose of a first substance from a syringe to a patient may be provided. The method may include: providing the syringe that comprises a syringe barrel; providing a first substance to the syringe barrel having an initial dose value; and mixing a second substance with the first substance in the syringe barrel to form a solution to be administered to the patient. Once the substances are mixed, the syringe may be primed by advancing a piston or plunger through the syringe barrel to expel a volume of the solution to the fluid path element. A total volume ($V_{Total}$) consisting of a volume of the first substance and a volume of the second substance based on a level of the solution remaining in the syringe barrel may be then determined. A dose volume ($V_{Dose}$) to be delivered to the patient based on a desired actual dose value of the first substance, a current dose value, and the total volume ($V_{Total}$) may be then calculated. Once the dose volume ($V_{Dose}$) is calculated, the piston or plunger may be advanced through the syringe barrel to expel the dose volume ($V_{Dose}$) from the syringe barrel.

According to another aspect of the disclosure, a fluid delivery system may be provided. The system may include: a fluid reservoir containing a first substance having an initial dose value and a second substance; a fluid conduit for directing at least a portion of the first substance and the second substance to a patient; and a fluid delivery device for expelling fluid from the fluid reservoir to the patient. The system may also include a controller configured to determine a maximum deliverable dose capable of being delivered to the patient. The controller may calculate the maximum deliverable dose based on a current dose value and a ratio of a deliverable volume ($V_{Deliverable}$) and a total volume ($V_{Total}$) consisting of a volume of the first substance and a volume of the second substance.

These and other features and characteristics of certain and non-limiting embodiments, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure. As used in the specification and the claims, the singular form of "a", "an", and "the" include plural referents unless the context clearly dictates otherwise.

BRIEF DESCRIPTION OF THE DRAWINGS

Further features and other objects and advantages will become apparent from the following detailed description made with reference to the drawings in which:

FIG. 3A is an illustration of a spreadsheet showing an exemplary implementation of the method of FIG. 2;

FIGS. 3B and 3C are illustrations of a spreadsheet showing algorithms used to calculate the values listed in the spreadsheet of FIG. 3A;

DETAILED DESCRIPTION

Figure 1:
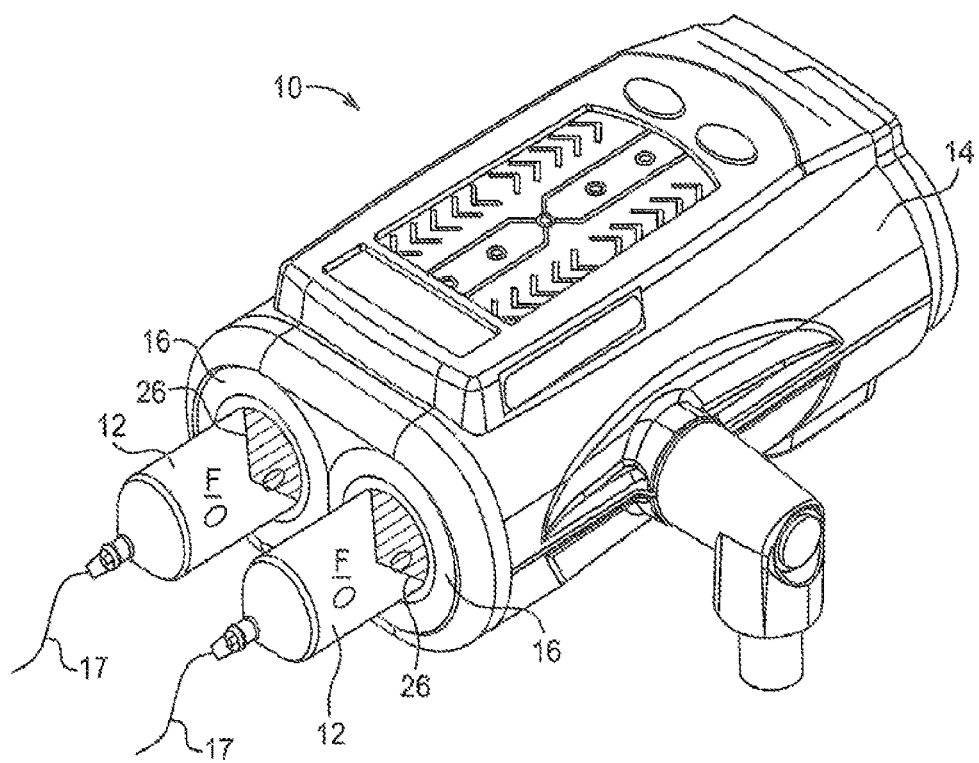
FIG. 1 is a perspective view of a power injector.

For purposes of the description hereinafter, the terms "end", "upper", "lower", "right", "left", "vertical", "horizontal", "top", "bottom", "lateral", "longitudinal", and derivatives thereof shall relate to various elements as they are oriented in the drawing figures. However, it is to be understood that the various elements may assume various alternative variations and step sequences, except where expressly specified to the contrary. It is also to be understood that the specific devices and processes illustrated in the attached drawings, and described in the following specification, are simply exemplary embodiments of the disclosure. Hence, specific dimensions and other physical characteristics related to the embodiments disclosed herein are not to be considered as limiting.

As used herein, the terms "communication" and "communicate" refer to the receipt or transfer of one or more signals, messages, commands, or other type of data. For one unit or component to be in communication with another unit or component means that the one unit or component is able to directly or indirectly receive data from and/or transmit data to the other unit or component. This can refer to a direct or indirect connection that may be wired and/or wireless in nature. Additionally, two units or components may be in communication with each other even though the data transmitted may be modified, processed, routed, and the like, between the first and second unit or component. For example, a first unit may be in communication with a second unit even though the first unit passively receives data, and does not actively transmit data to the second unit. As another example, a first unit may be in communication with a second unit if an intermediary unit processes data from one unit and transmits processed data to the second unit. It will be appreciated that numerous other arrangements are possible.

Fluid Injector

With reference to FIG. 1, a fluid injector 10 (hereinafter referred to as "injector 10"), such as an automated or powered fluid injector, is illustrated. The injector 10 may be adapted to interface with and actuate one or more syringes 12, which may be filled with a medical fluid F, such as contrast media, saline solution, or any desired medical fluid. The injector 10 may be used during a medical procedure to inject the medical fluid into the body of a patient by driving a plunger 26 of the syringe 12 with a piston element of the injector 10. The injector 10 may be a multi-syringe injector, wherein several syringes 12 may be oriented in a side-by-side or other relationship and are separately actuated by respective linear actuators or piston elements associated with the injector 10, and which engage plungers 26 disposed in the syringe 12. The injector 10 may be configured to independently deliver one or more fluids from the at least one syringe 12.

The injector 10 may be enclosed within a housing 14 formed from a suitable structural material, such as plastic or metal. The housing 14 may be of various shapes and sizes depending on the desired application. For example, the injector 10 may be a free-standing structure configured to be placed on the floor or may be a smaller design for placement on a suitable table or support frame. The injector 10 includes at least one syringe port 16 for connecting the at least one syringe 12 to respective piston elements. In some aspects, the syringe 12 includes at least one engagement member configured for retaining the syringe 12 within the syringe port 16 of the injector 10. The at least one engagement member is configured to operatively engage a locking mechanism provided in the syringe port 16 of the injector 10 to facilitate loading or removal of the syringe 12 to and from the injector 10, including ejecting the syringe 12 from the syringe port 16. The at least one engagement member and the locking mechanism together define a connection interface for releasably connecting the at least one syringe 12 to the injector 10.

A fluid path element 17 may be fluidly connected with at least one of the at least one syringe 12 for delivering medical fluid F from the at least one syringe 12 to a catheter (not shown) inserted into a patient at a vascular access site. Fluid flow from the at least one syringe 12 may be regulated by a fluid control module (not shown). The fluid control module operates various pistons, valves, and flow regulating structures to regulate the delivery of the medical fluid, such as saline solution and contrast to the patient based on user selected injection parameters, such as injection flow rate, duration, total injection volume, and ratio of contrast media and saline. A suitable front-loading fluid injector for use with the above-described system is disclosed in U.S. Pat. No. 5,383,858 to Reilly et al. which is incorporated by reference in its entirety. Other relevant multi-fluid delivery systems are found in U.S. Pat. No. 7,553,294 to Lazzaro et al.; U.S. Pat. No. 7,666,169 to Cowan et al.; International Patent Application No. PCT/US2012/037491, (published as WO 2012/155035); and United States Patent Application Publication No. 2014/0027009 to Riley et al.; all of which are assigned to the assignee of the present application, and the disclosures of which are incorporated herein by reference. A power injector that can be used with the methods and systems of the present disclosure is, for example, the Spectris Solaris EP Injection System manufactured by Bayer Healthcare of Pittsburgh, Pa.

Delivery Volume Calculation Method

Having described a suitable fluid or power injector 10 for injecting a fluid volume to a patient, a method for calculating and delivering a partial diluted dose of a fluid to be delivered or injected will now be discussed in detail. The method may be carried out using the injector 10 illustrated in FIG. 1. Alternatively, various hand injectors, syringes, reconstitution devices, autoinjectors, pen injectors, and the like may be used for delivering the diluted partial dose. In other aspects, the method may be used to fill a pharmaceutical container, such as a medical vial or intravenous bag. In still other aspects, the method may be used to calculate a diluted partial dose of a reconstituted drug, such as insulin.

Figure 2:
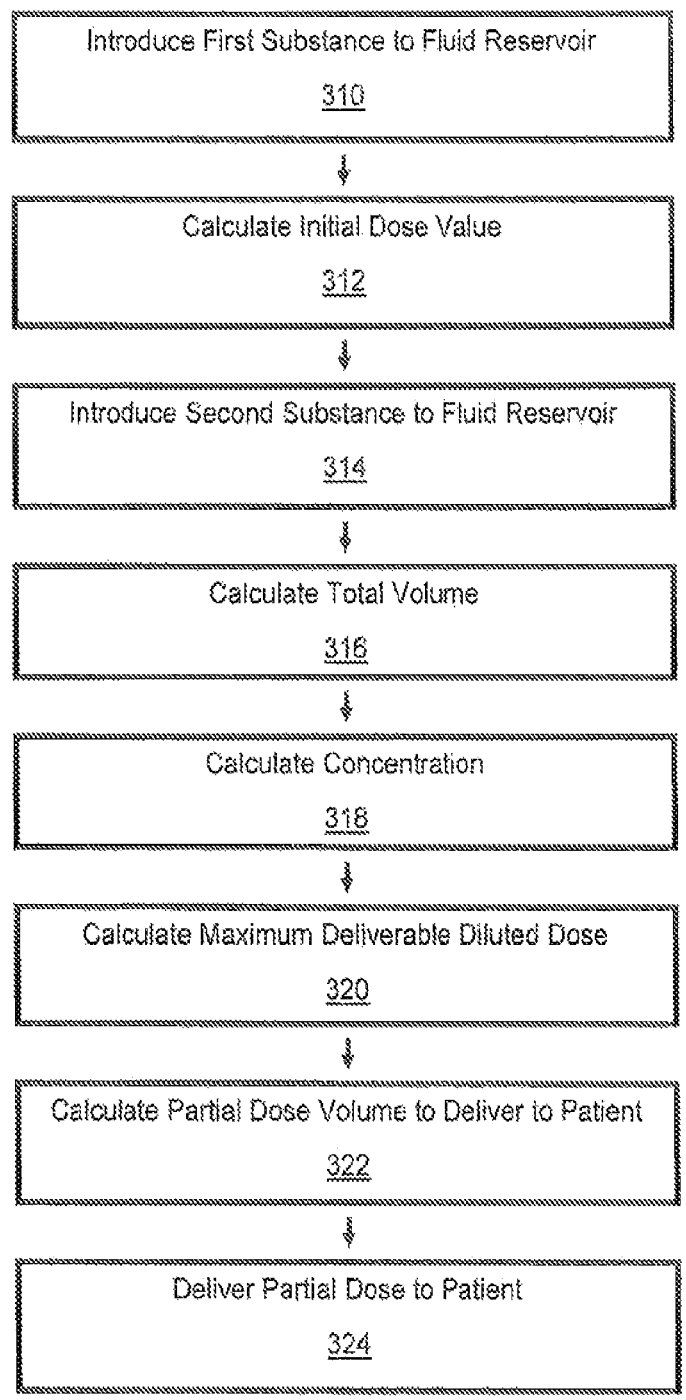
FIG. 2 is a flow chart illustrating a method of delivering a partial diluted dose to a patient, according to an aspect of the disclosure.

With reference to FIG. 2, a flow chart illustrating a method for delivering a partial diluted dose to a patient from a fluid reservoir, such as a syringe barrel, is provided. The method includes an initial or first step of providing or introducing a first substance to a fluid reservoir at operational block 310 in FIG. 2.

The first substance may be a therapeutic agent or drug, a contrast agent, a radioactive agent, a nutrient substance, or a biologically active agent. The drug or dose may come directly from a manufacturer or pharmacy and may not require further preparation by an operator, technician, or other health care professional prior to introducing the dose to the fluid reservoir. Based on the drug or dose, a unit dose quantity, which is referred to hereinafter as the initial dose value, is either known or calculated at operational block 312 in FIG. 2. The initial dose value may be a mass of the substance (e.g., 5 mg of drug). Alternatively, for a radioactive drug or radioactive agent, the initial dose value is radioactivity in mCi (milliCuries) or MBq (megaBecquerel). For biological agents used in cell therapy, the initial dose value may be expressed as a discrete number of live cells. In other aspects, some unit related to the number of molecules and/or biological equivalence or effectiveness of the drug, as in insulin, may also be used. In other aspects, the initial dose value is calculated from a known or measured volume of drug or dose ($V_{InitialDose}$) and a known or measured dose concentration ($C_{InitialDose}$) according to the equation Initial dose value=$V_{InitialDose}*C_{InitialDose}$. The measurement of volume of the drug may be done prior to placing it in the reservoir, or it may be done by the injector as part of the process of pulling it into the injector.

The first substance is mixed with or diluted by introducing a second substance to the fluid reservoir at operational block 314 in FIG. 2. The volume of the second substance does not need to be known. The second substance is often a diluent, such as saline or distilled water. However, any suitable substance for diluting or mixing with the first substance may be used. Mixing may be performed by shaking the fluid reservoir, by repeatedly inverting the fluid reservoir, with various mechanical mixing apparatus, by allowing diffusion to happen over a sufficient time, or by any other suitable mixing means. In addition, the order of adding the fluids to the reservoir is not critical, unless the reservoir is being used to measure the volume of the first fluid. For example, step 314 may occur before steps 310 and 312.

Once the first substance and the second substance are suitably mixed together, a total volume $V_{Total}$ of the first substance and the second substance is calculated at operational block 316 in FIG. 2. Since the volume of the first and/or second substance is not known, the total volume $V_{Total}$ must be measured directly. As described herein, the total volume may be measured automatically with a sensor positioned adjacent to the fluid reservoir. Alternatively, the total volume $V_{Total}$ may be measured by a user, such as by viewing a position of the solution relative to graduated markings on the fluid reservoir. The user may then enter or record the total volume $V_{Total}$ using a data entry accessory, keyboard, or user interface associated with the injector or another electronic device.

Once the total volume $V_{Total}$ is determined, a concentration of the first substance relative to the total volume $V_{Total}$ can be calculated at operational block 318 in FIG. 2. In addition, a maximum deliverable dose can be calculated at operational block 320. The maximum deliverable dose is defined as the maximum dose value or unit value of the first substance that can be delivered to the patient from the fluid reservoir. As described above, fluid delivery systems generally have a priming or non-deliverable volume that cannot be expelled from the reservoir and/or fluid path and thus cannot be delivered to the patient. The maximum deliverable dose is calculated based on a dose value and a ratio of a deliverable volume ($V_{Deliverable}$) and the total volume ($V_{Total}$). The deliverable volume ($V_{Deliverable}$) is equal to the total volume ($V_{Total}$) minus a non-deliverable volume ($V_{Non-deliverable}$). Alternatively, or in addition to calculating a maximum deliverable dose, a partial diluted dose volume $V_{PartialDose}$ to be delivered to a patient may also be calculated at operational block 322 in FIG. 2. The partial diluted dose volume $V_{PartialDose}$ is based on a desired, programmed, or prescribed dose to be delivered, a current dose value, and the total volume $V_{Total}$. In cases where the first substance does not degrade or decay, the dose value for the first substance is a constant. However, in situations where the first substance decays with time, such as for radioactive material or live cells, the dose value may change as time elapses. Accordingly, as described herein, various algorithms or models may be applied to calculate a time dependent Current dose value. The maximum deliverable dose and partial diluted dose are updated with time based on the Current dose value.

Once the partial diluted dose volume $V_{PartialDose}$ is calculated, the dose may be delivered to the patient 324, provided that the partial dose volume $V_{PartialDose}$ does not exceed the maximum deliverable dose. In some aspects, if the partial dose volume $V_{PartialDose}$ exceeds the maximum deliverable dose, the injector may provide a message or warning to the user indicating that the requested dose delivery cannot be completed. The user may redo the procedure or may choose to override that warning and deliver the maximum deliverable dose even though it is less than the desired dose. In a further embodiment, the user may choose to add additional volumes of the first fluid, the second fluid, or a third fluid to increase the dose and/or the total volume and recompute the maximum deliverable dose which will have increased.

It is understood that the methods and algorithms described herein may be incorporated into a controller comprising transitory or non-transitory computer memory and one or more associated processors. The controller may be integrally associated with the injector 10. The controller may also be associated with a dedicated electronic device or user interface device for assisting a user in the delivery of the substance to a patient. Alternatively, the controller may be associated with a remote electronic device, such as a personal computer, tablet PC, smart phone, or multi-purpose data accessory device capable of communicating data and instructions to and from the injector.

EXAMPLES

With reference to FIGS. 3A, 3B, and 3C, an exemplary scenario for diluting a dose of a drug and delivering a portion of the diluted dose to a patient will now be described. FIG. 3A is an illustration of a spreadsheet listing values calculated in the scenario; FIGS. 3B and 3C show the formulas used to calculate values shown in FIG. 3A. The letter-number designations in the discussion refer to cells on the spreadsheet. As shown in FIG. 3A, the initial volume of the drug is 2 ml B4 and the initial dose value is 9 mg B5. The concentration is 4.5 mg/ml B6. If the volume of the diluent is known or can be accurately measured, in this case 9 ml B7, then the total volume $V_{Total}$ is also known to be 11 ml B8. It is possible to do a dilution using pipettes to accurately measure volumes involved or scales to measure the weight of fluid added. In this example, the total volume and concentration can both be determined accurately.

Figure 4A:
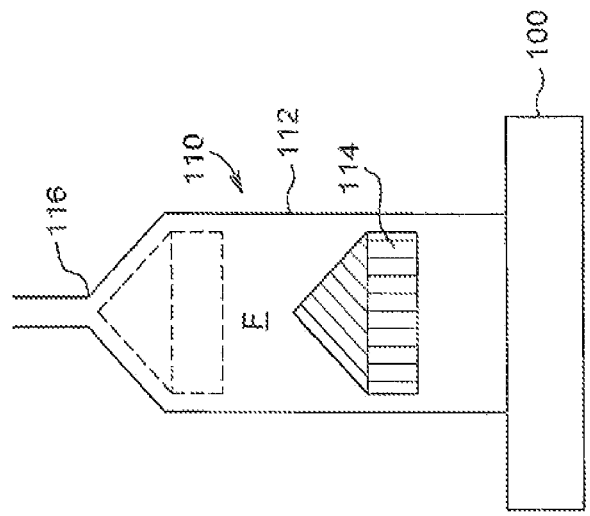
FIG. 4A is a schematic drawing of a syringe attached to a fluid injector, according to an aspect of the disclosure.
Figure 4B:
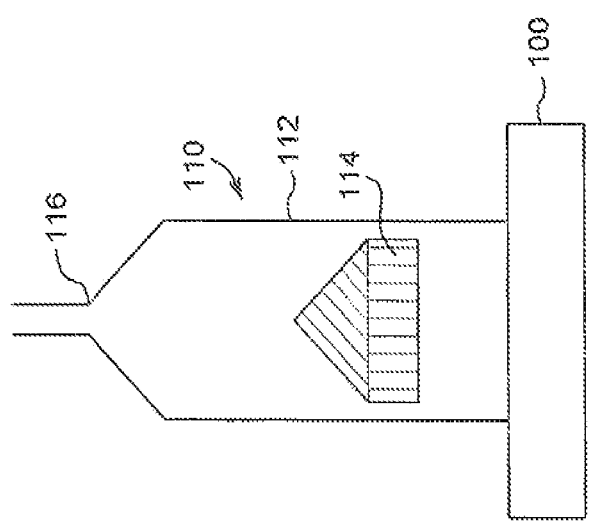
FIG. 4B is a schematic drawing showing the syringe and fluid injector of FIG. 4A filled with a fluid solution to be injected.
Figure 4C:
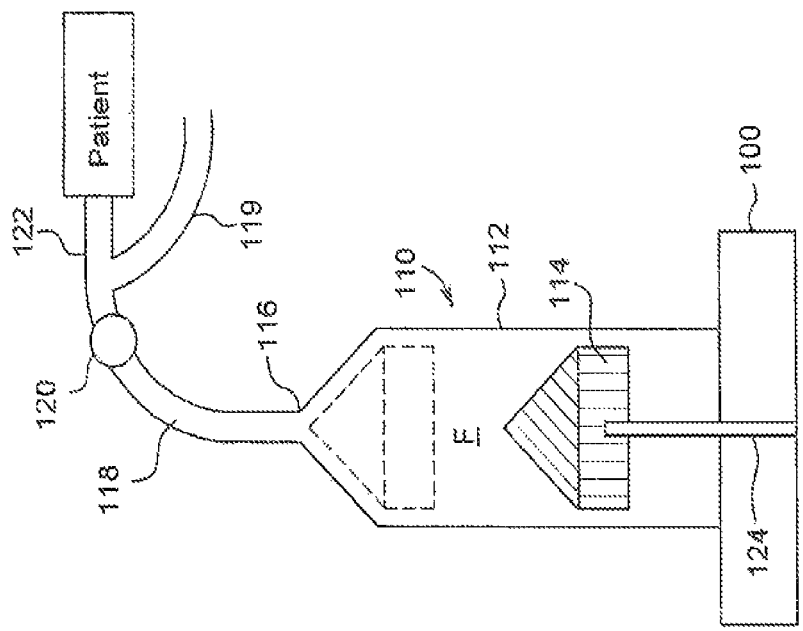
FIG. 4C is a schematic drawing of the syringe and fluid injector of FIG. 4A connected to a fluid path element for delivery to a patient.

With reference to FIGS. 4A and 4B, to deliver an accurate dose to the patient, an initial dose of the first substance and a volume of the diluent second substance are placed in a syringe barrel 112 of a syringe 110 to form a fluid solution F. In this example embodiment, the fluid conduit for the first fluid, the second fluid, and the diluted fluid all include at least the neck of the syringe 116. Additional fluid path elements known to those skilled in the art, for example tubes, spikes, valves, and connectors, may be used to deliver the fluids into the reservoir through the neck. If the reservoir is an alternative container or a syringe with multiple necks or ports, there may be two or more fluid conduits for fluid delivery into and out of the reservoir. The syringe 110 may be connected to a power injector 100. As shown in FIG. 4C, one or more fluid path elements, 118, 119, 120, and 122 may be connected to the syringe to conduct the fluid from the one or more reservoirs to the patient. If there is a single syringe reservoir, then the non-deliverable volume extends to the final delivery point to the patient and the fluid path can be very simple, for example, a needle, catheter, or a line and a vascular access device. If there is an additional fluid used for flushing some segment of the fluid path, there will be another fluid path element 119 which is used to conduct the flushing fluid to and through the final fluid path segment 122. The flushing fluid is commonly delivered after the delivery of the diluted fluid. One benefit of having a flushing fluid is that the dead volume is only determined by the dead volume of the syringe and the fluid path element or elements before the junction with the flushing fluid path 119, in this example embodiment that is fluid path elements 118 and 120. This can significantly reduce the total dead volume. An additional benefit is that the flushing fluid may be used to prime the system during initial setup.

A plunger 114 is moved forward to prime the full dead or non-deliverable volume $V_{Non\text{-}deliverable}$, by directing fluid to the syringe nozzle 116 and fluid path element 118, as shown in FIG. 4C. More specifically, the primed fluid flows from the syringe barrel 112, through the nozzle 116, and to a check valve 120 in the fluid path element 118. The check valve 120 is in fluid communication with any additional fluid path elements 122, for example a coiled connector tube and a catheter, for delivering the fluid to a patient. In some aspects, a user interface or visual display associated with the injector 100 then provides a read-out of the deliverable volume $V_{Deliverable}$, which is presented in B11 of FIG. 3A. Thus, in this example, the prime volume is 1 ml. The concentration can be computed from the initial dose value and total volume $V_{Total}$ either manually or automatically by the injector 100. To deliver a desired dose, the dose volume is determined by dividing the desired dose value by the concentration.

In another example, where a radioactive drug is to be diluted, a radioactive drug of known activity is provided (e.g., in mCi). The drug may be provided in, for example, a hand syringe. The actual volume of the drug is usually not controlled or known, but can only be assessed roughly using markings on the hand syringe. To inject a dose of the radioactive drug using a power injector, such as the injector 100 illustrated in FIGS. 4A-4C, the drug fluid from the hand syringe is transferred into a syringe 110. Then additional diluent is provided as show in FIGS. 4B and 4C to form fluid solution F. Preferably the syringe 110 is then moved or shaken to agitate the fluid and promote uniform mixing of the fluid solution F. This results in a known quantity of drug (e.g., the initial dose), but in an unknown quantity of fluid (e.g., total volume). Alternatively, the order in which the first fluid and the second fluid are provided to the syringe 110 may be reversed. For example, as described herein, the syringe 110 may be first filled with the second fluid, the diluent, and then the first fluid, the dose can be added. In addition, the fluids may be added simultaneously, which helps promote mixing, or in one or more steps or partial volumes, which may be interleaved with each other as the user desired. Once both fluids are added, the solution is mixed as described herein.

The total volume $V_{Total}$ can be determined as follows. First, the syringe 110 is connected to the injector 100. At this point during operation, the injector 100 can provide a readout of deliverable volume remaining in the syringe, which is determined by measuring the position of the injector head piston 124 (shown in FIG. 4C) in comparison to the known maximum forward or maximum delivered volume position of the piston 124. The syringe plunger 114 is then engaged with the piston 124. As shown in FIG. 4C, the remainder of the fluid path elements, specifically the check valve 120 and associated tubing, are connected onto the syringe nozzle 116. The piston 124 and syringe plunger 114 are then moved forward, causing the drug to move into the syringe nozzle 116 and to the check valve 120, thereby filling the dead space or non-deliverable volume $V_{NonDeliverable}$ in the fluid path element 118. The forward movement is preferably stopped just before any drug fluid moves through the check valve 120.

The dead space or non-deliverable volume $V_{NonDeliverable}$ B11 (shown in FIG. 3A) is determined based on the geometries of these fluid path elements, and can be known if the standard fluid path elements are used. Alternatively, the user may enter this information on the dead space or non-deliverable $V_{NonDeliverable}$ if non-standard fluid path elements are being used. As another option, the fluid path elements may have an associated information element, such as a bar code or QR code, which can communicate information to the injector to select the proper dead space volume to use.

At this point, the volume remaining readout (B10) (in FIG. 3A) of the injector 100 represents the fluid that can be delivered from the syringe 110 to the patient (e.g., $V_{Deliverable}=V_{Total}-V_{NonDeliverable}$). The total volume $V_{Total}$ is listed at B13. The diluted concentration can be calculated according to the equation Concentration=Drug Dose/$V_{Total}$. The Concentration is listed at (B14).

The maximum deliverable dose value (referred to hereinafter as "MaxDeliverableDose") that is available for injection, which is listed in B15, is calculated according to one of the following equations:

MaxDeliverableDose=$V_{Deliverable}$*Concentration;

MaxDeliverableDose=Drug Dose*($V_{Deliverable}/V_{Total}$); or

MaxDeliverableDose=Drug Dose*($V_{Deliverable}/(V_{Deliverable}+V_{NonDeliverable})$).

MaxDeliverableDose=Drug Dose*($V_{Total}-V_{NonDeliverable}/V_{Total}$).

The Drug Dose may be the initial dose value (e.g., the quantity of the first substance or drug) in situations in which the dose does not degrade or decay. To deliver a dose less than the MaxDeliverableDose, the injector 100 delivers a volume B17 computed by using a desired actual dose divided by the diluted concentration B14.

In an additional embodiment, if the maximum deliverable dose is not sufficient to proceed with the procedure, an additional dose may be added to the reservoir by adding an additional volume of the first fluid, in which case the new initial dose becomes the sum of the one or more doses put in the reservoir, and the procedure described herein can be repeated to determine the new fluid and system values, for example of concentration, maximum deliverable dose, and other values mentioned herein.

In a further embodiment, if the maximum deliverable dose is not sufficient to proceed with the procedure, although the current total drug dose is sufficient, an additional volume of diluent, for example the second fluid, may be added to this reservoir. This increases the maximum deliverable dose by increasing the total volume in comparison to the non-deliverable volume.

In a further example situation in which the drug is a radioactive isotope, contains live cells that may die over time, or contains some other substance that changes over time, the decay of the dose or activity may be modeled. Further, in situations in which multiple injections are performed, the change in dose over time, due to decay, can be calculated and accounted for. For example, decay may be modeled using a known or determinable half-life or a predicted cell lifespan. In this case, the drug dose is presented as a Current dose value that decreases with respect to time. Since the Current dose value varies, the volume to be injected also changes over time in the situation where it is desirable to inject a constant dose. Further, as will be appreciated by one with ordinary skill in the art, there will come a time when the activity has decayed sufficiently that the desired dose can no longer be delivered (e.g., the desired dose≥the maximum deliverable dose).

An example of this application is shown in FIG. 3A, rows 22 through 30. Particularly, B22 on FIG. 3A shows that the half-life for the radioactive substance is 6 hours and 21 seconds. The Initial Dose Value was measured at 10:30, as shown at B23 on FIG. 3A. The radioactive agent or drug was diluted or mixed with a second substance. The system was ready to perform the injection starting at 11:00, as shown at B26 on FIG. 3A. In this example, it has been decided to recalculate the volume to be delivered every hour. This results in a decay from the beginning of a time period to the end of the time period of 0.891, as shown at B25 on FIG. 3A.

In this example, the units for the dose value are mCi rather than mg. As shown at B16, the desired maximum dose is 5 mCi. The example computations of Volume to Inject, listed at D26:D30 on FIG. 3A, are computed at respective different times, B26:B30 on FIG. 3A, using the formula in D26:D30 on FIG. 3C. In this example, the maximum desired dose B16 on FIG. 3A would be given at the beginning of the time period; the dose at the end of the time period would be 0.891, as shown at B25 on FIG. 3A.

Alternatively, if the desired dose, B16 on FIG. 3A, were to be the minimum desired dose, then the volume for the next time period could be used. For example, during the first hour from 11:00 to 12:00, using a volume of 7.27, as shown at B27 on FIG. 3A, would ensure that at least 5 mCi were injected during that first hour.

Another option, not illustrated in FIGS. 3A, 3B, and 3C, is to change the volume so that initially the dose is greater than the desired dose by an amount such that at the end of a predetermined time period, the current dose value is equal or substantially similar to a desired dose. As will be appreciated by one having ordinary skill in the art, as the time increment or delay is shortened, the difference between the dose delivered at the beginning and at the end of the injection period decreases.

In a scenario in which each injection is being performed manually by an operator or technician, rather than controlled automatically by the injector 100, the time change increment or period between injections should not be too short or it will become a burden on the operator. Preferably, a one hour time period is a reasonable time for a half-life of 6 hours. In an application where this algorithm or program is implemented in the injector itself, it can be updated every minute or even faster with little or no hardship to the operator. The injector display simply displays the volume that will be injected if it is triggered at that time.

In both cases, there will come a time when the activity has decayed to a point that the desired dose cannot be delivered (e.g., current dose value<max deliverable dose). An example of this situation is illustrated in the last time increment, row 30 (cells A30 to F30) on FIG. 3A, in which injecting the full available volume of 10 ml D30, only delivers a maximum of 4.87 mCi, F30, at or after 15:00:00 B30.

Fluid Injection System

Having described various methods for calculating and delivering partial diluted doses of drugs and other substances, a fluid injection system capable of carrying out the above-described methods is now discussed in detail.

Figure 5:
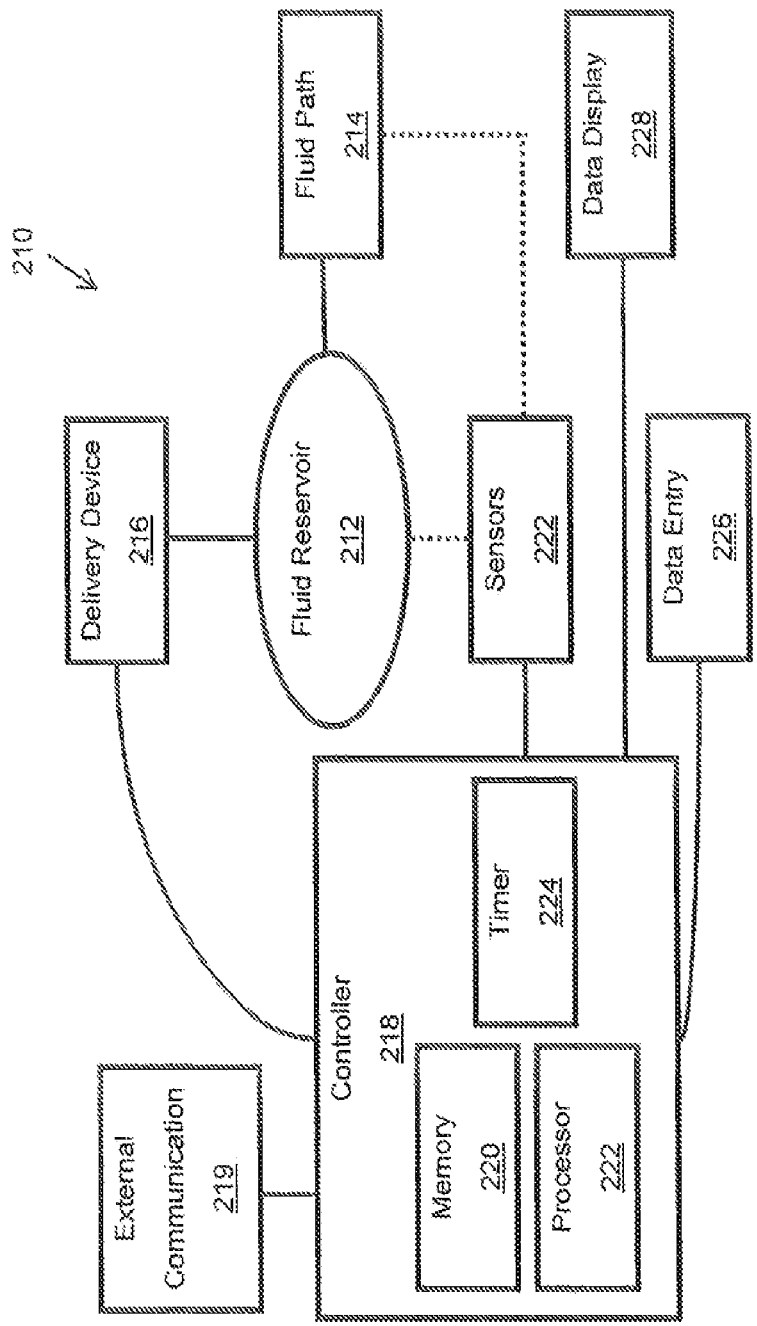
FIG. 5 is a block diagram of a fluid delivery system, according to an aspect of the disclosure.

With reference to FIG. 5, the system 210 includes at least one fluid reservoir 212 in fluid communication with a fluid path element 214 and/or catheter, which may include flexible plastic tubing and one or more check valves or manifolds for controlling fluid delivery. The fluid path element 214 defines a dead or non-deliverable volume $V_{NonDeliverable}$. The fluid reservoir 212 defines a deliverable volume capable of being expelled from the reservoir 212 and delivered to a patient. The system 210 also includes a fluid delivery device 216 for expelling fluid from the fluid reservoir 212. The fluid delivery device 216 may be a power injector or hand injector capable of driving a piston and/or plunger through the reservoir 212 to expel fluid therefrom.

Various pneumatic, peristaltic, or infusion pumps may also be used for this purpose. The fluid delivery device 216 may be controlled with a controller 218, including memory 220 for storing instructions for operation of the device 216 and a processor 222 for implementing the instructions. More specifically, the controller 218 may be configured to calculate the Total Volume $V_{Total}$, Concentration, MaxDeliveryDose, Dose Volume, and/or Current dose value according to the above-described methods and algorithms. Once the Dose Volume is calculated, the controller 218 may also be configured to provide instructions to the fluid delivery device 216 for expelling the appropriate fluid volume from the reservoir 212 through the fluid path element 214, and to the patient.

In some aspects, one or more sensors 222 are associated with the fluid reservoir 212 and/or fluid path element 214. The sensors 222 are in electrical communication with the controller 218 for sending information thereto. In some aspects, the sensors 222 measure the position of a piston of the fluid delivery device 216. In other aspects, the sensors 222 may measure a fluid level in the fluid reservoir 212. For example, a sensor 222 may be positioned to determine the level of the meniscus of the fluid solution in the reservoir 212. Appropriate sensors for measuring fluid level include a pressure sensor, ultrasonic sensor, an RF sensor, a conductivity sensor, an optical sensor, other types of sensors know in the art for measuring the presence, property, or absence of a fluid, or any combination thereof. In a further embodiment, the operator's eye may be a sensor, for example the operator may control the movement or presence of a meniscus to or at a certain point in the fluid path by manually or through a button advancing the syringe plunger, or the operator may simple indicate when a meniscus gets to a certain point as the injector slowly advances the fluid. The operator may communicate to the system through one or more aspects of the data entry subsystem 226. Data obtained from the sensors 222 can be used for determining the total volume $V_{Total}$ of the diluted fluid within the reservoir 212.

In some aspects, the controller 218 may also include or be associated with a timer 224 for determining an elapsed time value. The timer 224 may be used to determine a decay time for the drug or substance contained in the fluid reservoir 212. The timer 224 may, for example, be a clock and the elapsed time is computed by comparing the time at which the initial dose was measured to the current time. As described above, the decay time may be used to determine a Current dose value for substances that decay or degrade over time. A decay rate or cell death rate may be stored in the controller memory 220. The controller 218 may be configured to obtain the decay rate for a particular substance from the memory 220 and calculate the Current dose value, based on a time provided by the timer 224. The current dose value may be updated continually by the controller 218 or at predetermined intervals, such as every 5 minutes. As described in the examples above, the current dose value is used to update the MaxDeliveryDose and Dose Volume by taking into account the substance decay.

In some aspects, a data entry panel 226 may also be provided to allow a user to manually enter known values. For example, a user may be required to manually enter the dead space or non-deliverable volume $V_{NonDeliverable}$ to the controller 218 before the concentration and MaxDeliveryDose can be calculated. The data entry panel 226 may be a series of buttons or keys on the injector itself. Alternatively, a keyboard, computer mouse, trackball, or other data entry accessory may also be used for this purpose. In other aspects, the system 210 may include a display or output device 228 for providing calculated values, for example maximum deliverable dose, for review by the operator and for feedback to the operator when entering known or determined values, for example, for use by the controller 218, and for informing the operator of the status and operational condition and state of the system 210. The output device 228 may also comprise, for example, audible alarms, visible indicators, and other sensory outputs know to those in the human factors arts to communicate information to the operator.

Computer System or Device

Figure 6:
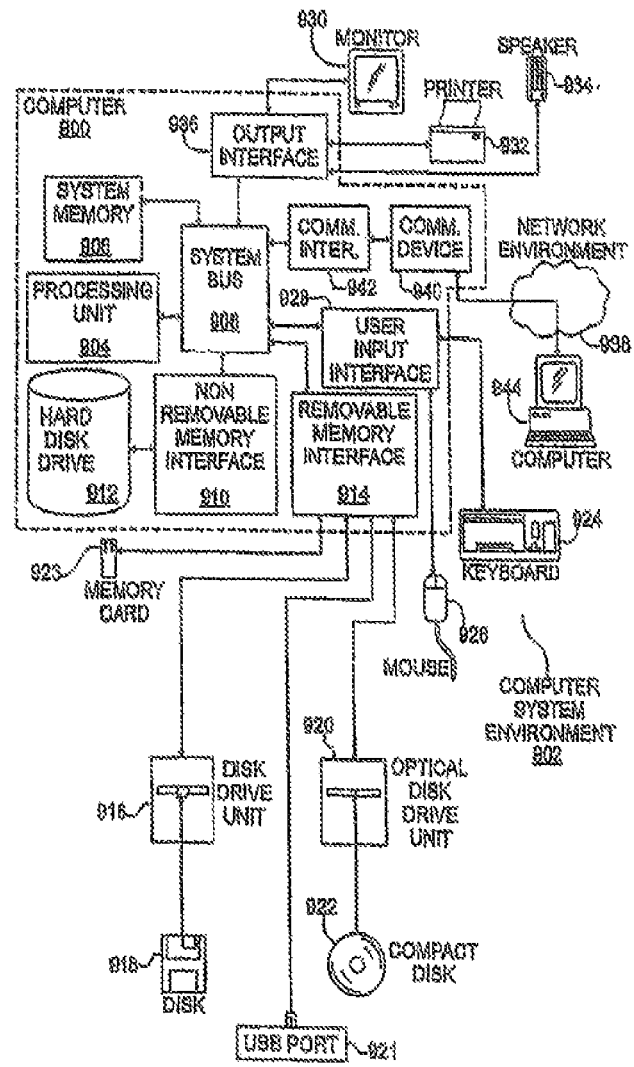
FIG. 6 is a block diagram of an example computer system, according to aspects of the disclosure.

As previously noted, various aspects of the above described methods and algorithms may be implemented on a variety of computing devices and systems which may or may not be integrally connected to the injector itself. For example, the above-described processes and algorithms may be implemented on any sort of a remote computing device, such as a personal computer, which includes appropriate processing mechanisms and computer-readable media for storing and executing computer-readable instructions, such as programming instructions, code, and the like. As shown in FIG. 6, personal computers 900, 944, in a computing system environment 902 are provided. This computing system environment 902 may include, but is not limited to, at least one computer 900 having certain components for appropriate operation, execution of code, and creation and communication of data. For example, the computer 900 includes a processing unit 904 (typically referred to as a central processing unit or CPU) that serves to execute computer-based instructions received in the appropriate data form and format. Further, this processing unit 904 may be in the form of multiple processors executing code in series, in parallel, or in any other manner for appropriate implementation of the computer-based instructions.

In order to facilitate appropriate data communication and processing information between the various components of the computer 900, a system bus 906 is utilized. The system bus 906 may be any of several types of bus structures, including a memory bus or memory controller, a peripheral bus, or a local bus using any of a variety of bus architectures. In particular, the system bus 906 facilitates data and information communication between the various components (whether internal or external to the computer 900) through a variety of interfaces, as discussed hereinafter.

The computer 900 may include a variety of discrete computer-readable media components. For example, this computer-readable media may include any media that can be accessed by the computer 900, such as volatile media, non-volatile media, removable media, non-removable media, etc. As a further example, this computer-readable media may include computer storage media, such as media implemented in any method or technology for storage of information, such as computer-readable instructions, data structures, program modules, or other data, random access memory (RAM), read only memory (ROM), electrically erasable programmable read only memory (EEPROM), flash memory, or other memory technology, CD-ROM, digital versatile disks (DVDs), or other optical disk storage, magnetic cassettes, magnetic tape, magnetic disk storage, or other magnetic storage devices, or any other medium which can be used to store the desired information and which can be accessed by the computer 900. Further, this computer-readable media may include communications media, such as computer-readable instructions, data structures, program modules, or other data in a modulated data signal, such as a carrier wave or other transport mechanism and include any information delivery media, wired media (such as a wired network and a direct-wired connection), and wireless media (such as acoustic signals, radio frequency signals, optical signals, infrared signals, biometric signals, bar code signals, etc.). Of course, combinations of any of the above should also be included within the scope of computer-readable media.

The computer 900 further includes a system memory 908 with computer storage media in the form of volatile and non-volatile memory, such as ROM and RAM. A basic input/output system (BIOS) with appropriate computer-based routines assists in transferring information between components within the computer 900 and is normally stored in ROM. The RAM portion of the system memory 908 typically contains data and program modules that are immediately accessible to or presently being operated on by the processing unit 904, e.g., an operating system, application programming interfaces, application programs, program modules, program data, and other instruction-based computer-readable codes.

With continued reference to FIG. 6, the computer 900 may also include other removable or non-removable, volatile or non-volatile computer storage media products. For example, the computer 900 may include a non-removable memory interface 910 that communicates with and controls a hard disk drive 912, e.g., a non-removable, non-volatile magnetic medium; and a removable, non-volatile memory interface 914 that communicates with and controls a magnetic disk drive unit 916 (which reads from and writes to a removable, non-volatile magnetic disk 918), an optical disk drive unit 920 (which reads from and writes to a removable, non-volatile optical disk 922, such as a CD ROM), a Universal Serial Bus (USB) port 921 for use in connection with a removable memory card, etc. However, it is envisioned that other removable or non-removable, volatile or non-volatile computer storage media can be used in the exemplary computing system environment 902, including, but not limited to, magnetic tape cassettes, DVDs, digital video tape, solid state RAM, solid state ROM, etc. These various removable or non-removable, volatile or non-volatile magnetic media are in communication with the processing unit 904 and other components of the computer 900 via the system bus 906. The drives and their associated computer storage media discussed above and illustrated in FIG. 6 provide storage of operating systems, computer-readable instructions, application programs, data structures, program modules, program data, and other instruction-based computer-readable code for the computer 900 (whether duplicative or not of this information and data in the system memory 908).

A user may enter commands, information, and data into the computer 900 through certain attachable or operable input devices, such as a keyboard 924, a mouse 926, etc., via a user input interface 928. Of course, a variety of such input devices may be utilized, e.g., a microphone, a trackball, a joystick, a touchpad, a touch-screen, a scanner, etc., including any arrangement that facilitates the input of data, and information to the computer 900 from an outside source. As discussed, these and other input devices are often connected to the processing unit 904 through the user input interface 928 coupled to the system bus 906, but may be connected by other interface and bus structures, such as a parallel port, game port, or a USB. Still further, data and information can be presented or provided to a user in an intelligible form or format through certain output devices, such as a monitor 930 (to visually display this information and data in electronic form), a printer 932 (to physically display this information and data in print form), a speaker 934 (to audibly present this information and data in audible form), etc. All of these devices are in communication with the computer 900 through an output interface 936 coupled to the system bus 906. It is envisioned that any such peripheral output devices be used to provide information and data to the user.

The computer 900 may operate in a network environment 938 through the use of a communications device 940, which is integral to the computer 900 or remote therefrom. This communications device 940 is operable by and in communication to the other components of the computer 900 through a communications interface 942. Using such an arrangement, the computer 900 may connect with or otherwise communicate with one or more remote computers, such as a remote computer 944, which may be a personal computer, a server, a router, a network personal computer, a peer device, or other common network nodes, and typically includes many or all of the components described above in connection with the computer 900. Using appropriate communication devices 940, e.g., a modem, a network interface or adapter, etc., the computer 900 may operate within and communicate through a local area network (LAN) and a wide area network (WAN), but may also include other networks such as a virtual private network (VPN), an office network, an enterprise network, an intranet, the Internet, etc. It will be appreciated that the network connections shown are exemplary and other means of establishing a communications link between the computers 900, 944 may be used.

As used herein, the computer 900 includes, or is operable to execute appropriate custom-designed or conventional software to perform and implement the processing steps of the method and system of the present disclosure, thereby forming a specialized and particular computing system. Accordingly, the presently-invented method and system may include one or more computers 900 or similar computing devices having a computer-readable storage medium capable of storing computer-readable program code or instructions that cause the processing unit 904 to execute, configure, or otherwise implement the methods, processes, and transformational data manipulations discussed hereinafter in connection with the present disclosure. Still further, the computer 900 may be in the form of a personal computer, a personal digital assistant, a portable computer, a laptop, a palmtop, a mobile device, a mobile telephone, a server, or any other type of computing device having the necessary processing hardware to appropriately process data to effectively implement the presently-invented computer-implemented method and system.

It will be apparent to one skilled in the relevant arts that the system may utilize databases physically located on one or more computers which may or may not be the same as their respective servers. For example, programming software on computer 900 can control a database physically stored on a separate processor of the network or otherwise.

Although the methods and systems have been described in detail for the purpose of illustration based on what is currently considered to be the preferred aspects, it is to be understood that such detail is solely for that purpose and that the disclosure is not limited to the disclosed aspects, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment and that the order of the steps in any methods may be interchanged to the extent that the results are the same. For example, at least one additional drug or diluent fluids may be used, with the ability to calculate the corresponding properties of the corresponding drug doses. In a further example, an embodiment may operate with two or more drugs, with no additional diluent. In an additional embodiment, the system and methods may be applied to dispense the diluted drug into one or more intermediate containers, for example syringes, vials, or bags, for subsequent delivery to one or more patients.

What is claimed is:

1. A method of determining a maximum deliverable dose or a non-deliverable dose in a fluid reservoir, the method comprising:
    providing a first substance within the fluid reservoir having an initial dose value;
    diluting the first substance with a second substance to produce a diluted solution;
    determining a total volume ($V_{Total}$) of the diluted solution;
    calculating the maximum deliverable dose or the non-deliverable dose within the reservoir based on the initial dose value and at least two of a deliverable volume ($V_{Deliverable}$), a non-deliverable volume ($V_{Non-deliverable}$), a concentration of the diluted solution, a total dose, and the total volume ($V_{Total}$)
    wherein the fluid reservoir is selected from the group consisting of a syringe barrel, a cartridge, a medical vial, an intravenous bag, a sample container, a length of tubing, and a pump reservoir.

2. The method of claim 1, wherein the initial dose value is selected from the group consisting of a mass or number of molecules of the first substance, a radioactivity of the first substance, a number of live cells present in the first substance, and a number of units of biological activity of the first substance.

3. The method of claim 1, further comprising calculating a current dose value based on the initial dose value, an elapsed time and a decay rate, or on an estimated lifespan of living cells of the first substance, wherein the decay rate is based on a half-life of a radioactive component of the first substance.

4. The method of claim 1, wherein the total volume ($V_{Total}$) is an initially unknown value and determinable based on a fluid level in a fluid path element.

5. The method of claim 4, further comprising automatically determining the fluid level based on data provided by one or more sensors.

6. The method of claim 5, wherein the one or more sensors comprise one or more sensors selected from the group consisting of an optical sensor, a pressure sensor, an ultrasonic sensor, a radio sensor, and any combination thereof.

7. A method for determining a maximum deliverable dose within a reservoir, the method comprising:
    providing a first substance within the reservoir having an initial dose value;
    introducing a second substance to the reservoir to produce a diluted solution;
    determining a total volume ($V_{Total}$), wherein the total volume is the sum of a volume of the first substance and a volume of the second substance;
    calculating the maximum deliverable dose within the reservoir based on the initial dose value and a ratio of a deliverable volume ($V_{Deliverable}$) and the total volume ($V_{Total}$), and
    delivering up to the maximum deliverable dose to a patient through a fluid delivery system,
    wherein the fluid delivery system comprises the reservoir and a fluid path element in fluid communication with the reservoir and configured for delivering fluid from the reservoir to the patient.

8. The method of claim 7, wherein the deliverable volume ($V_{Deliverable}$) is equal to the total volume ($V_{Total}$) less a non-deliverable volume ($V_{Non-deliverable}$).

9. The method of claim 8, wherein the non-deliverable volume ($V_{Non-deliverable}$) is measured by filling at least part of one or more fluid path elements connected to the reservoir with fluid from the reservoir and then measuring a remaining volume in the reservoir.

10. The method of claim 8, wherein the non-deliverable volume ($V_{Non-deliverable}$) is a known quantity based on shapes of the reservoir and one or more fluid path elements connected to the reservoir.

11. The method claim 10, wherein the non-deliverable volume ($V_{Non-deliverable}$) is defined by at least a portion of the fluid path element or the reservoir.

12. The method of claim 7, further comprising calculating a dose volume ($V_{Dose}$) based on a desired actual dose value of the first substance, the initial dose value, and the total volume ($V_{Total}$).

13. The method of claim 12, further comprising confirming that the dose volume ($V_{Dose}$) is less than or equal to the deliverable volume ($V_{Deliverable}$) of the reservoir.

14. A fluid delivery system comprising:
    a fluid reservoir configured for receiving a first substance having an initial dose value;
    a fluid conduit configured for introducing a second substance into the fluid reservoir to produce a diluted solution;
    a fluid delivery device having a fluid delivery conduit configured for delivering at least a portion of the diluted solution from the fluid reservoir to a patient; and
    a controller configured to determine a maximum deliverable dose capable of being delivered to the patient or non-deliverable dose that remains in the fluid reservoir,
    wherein the controller calculates the maximum deliverable dose or non-deliverable dose based on the initial dose value and at least two of a deliverable volume ($V_{Deliverable}$), a non-deliverable volume ($V_{Non-deliverable}$), a concentration of the diluted solution, a total dose, and a total volume ($V_{Total}$).

15. The system of claim 14, further comprising at least one sensor configured to provide information used to determine the total volume ($V_{Total}$) based on a fluid level in a fluid path element, wherein the at least one sensor is selected from the group consisting of an optical sensor, a pressure sensor, an ultrasonic sensor, a radio sensor, an optical sensor, a conductivity sensor, a fluid sensor, and any combination thereof.

16. The system of claim 15, wherein the at least one sensor is positioned to measure a position of a meniscus of the fluid solution contained within the fluid reservoir after priming of the fluid reservoir and the fluid conduit by the fluid delivery device.

17. The system of claim 14, wherein the fluid delivery device is selected from the group consisting of a hand injector, a power injector, an auto-injector, a gravity based drip mechanism, a pneumatic pump, a peristaltic pump, and an infusion pump.

18. The system of claim 14, wherein the controller comprises at least one non-transitory computer-readable storage medium in communication with one or more processors and having instructions stored thereon, which, when executed by the one or more processors, causes the one or more processors to:

determine the total volume ($V_{Total}$) of the first substance and the second substance based on data received from the one or more sensors; and calculate the maximum deliverable dose within the fluid reservoir based on a current dose value and a ratio of the deliverable volume ($V_{Deliverable}$) and the total volume ($V_{Total}$).

19. The system of claim 18, wherein the controller further causes the one or more processors to:

calculate the current dose value based on the initial dose value, elapsed time data obtained from a timer, and a decay rate.

20. The system of claim 14, wherein the controller is further configured to actuate the fluid delivery device to deliver a partial dose of the diluted solution to the patient, the partial dose being less than or equal to the maximum deliverable dose.

\* \* \* \* \*